Figure 1:
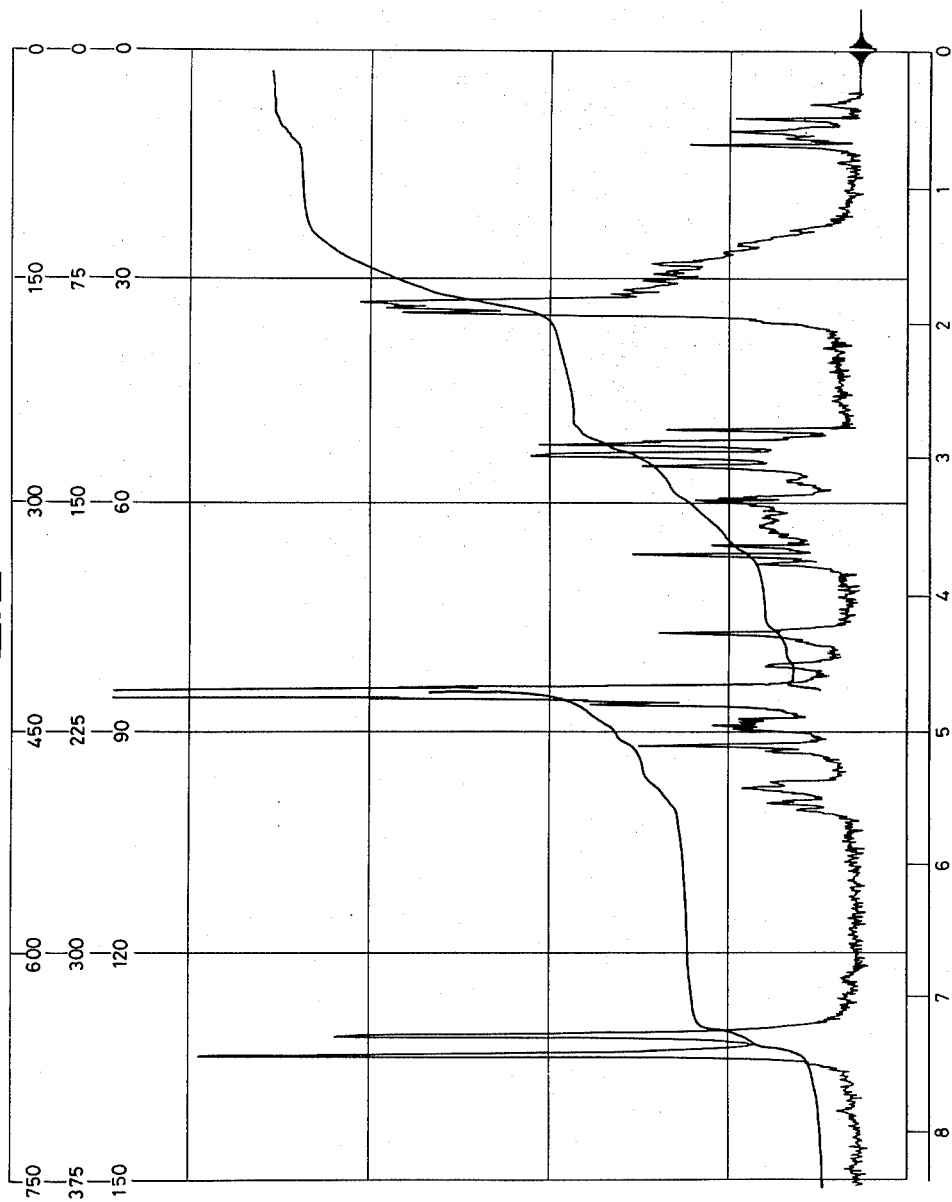

United States Patent [19]

Reiner

[11] Patent Number: 4,471,115
[45] Date of Patent: Sep. 11, 1984

[54] WATER SOLUBLE DERIVATIVES OF CEPHALEX AND PROCESS FOR THEIR PREPARATION

[75] Inventor: Alberto Reiner, Como, Italy

[73] Assignee: Neopharmed S.p.A., Baranzate di Bollate, Italy

[21] Appl. No.: 452,159

[22] Filed: Dec. 22, 1982

Related U.S. Application Data

[63] Continuation of Ser. No. 309,377, Oct. 7, 1981, abandoned.

[30] Foreign Application Priority Data

Oct. 13, 1980 [IT] Italy ................... 25267 A/80

[51] Int. Cl.$^3$ ................... C07D 501/04; C07D 501/22
[52] U.S. Cl. ................................................. 544/30
[58] Field of Search ........................................... 544/30

[56] References Cited

U.S. PATENT DOCUMENTS

| | | | |
|---|---|---|---|
| 3,634,417 | 1/1972 | Attenburrow | 544/30 |
| 3,741,963 | 6/1973 | Dursch et al. | 544/30 |
| 3,796,709 | 3/1974 | Breuer et al. | 544/30 |
| 3,880,842 | 4/1975 | Lee | 544/30 |
| 3,988,326 | 10/1976 | Seki et al. | 544/30 |

Primary Examiner—Paul M. Coughlan, Jr.
Attorney, Agent, or Firm—Murray and Whisenhunt

[57] ABSTRACT

The water soluble derivatives of cephalexin, having general formula:

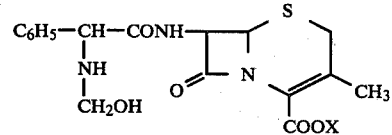

wherein X represents an alkali metal or the organic nitrogen containing cation of a basic aminoacid, combine the typical antibiotic action of cephalexin with the water solubility and form essentially neutral, aqueous solutions. The process for the preparation of the above derivatives comprises a first step in which the methylol derivative of cephalexin is prepared and a second step in which the treatment with a suitable base is carried out.

9 Claims, 2 Drawing Figures

WATER SOLUBLE DERIVATIVES OF CEPHALEX AND PROCESS FOR THEIR PREPARATION

This is a continuation application of Ser. No. 309,377, filed Oct. 7, 1981, now abandoned.

The present invention relates to novel derivatives of cephalexin soluble in water and thus useful also as injectable formulations, and to a process for their preparation.

The utility of cephalexin as a wide spectrum antibiotic and the relationship thereof with the antibiotics of the cephalosporin group are well known. Cephalexin is the generic name given to the 7-(D-2-amino-2-phenylacetamido)-3-methyl-$\Delta^3$-4-carboxylic acid, having the formula

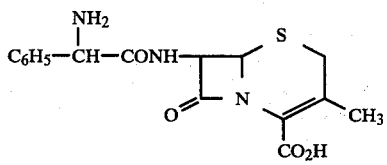

As it is well known, the cephalexin, as such, is insoluble in water and consequently can not be administered by direct injection.

On the other hand, the water soluble derivatives of cephalexin, known up to date, show in water solution a definitely alkaline pH.

Thus the main purpose of the present invention is that of providing cephalexin derivatives, which, besides maintaining the wide range of antibacterial activity of cephalexin, are water soluble and give essentially neutral water solutions. A further purpose of the present invention is that of providing a process for the preparation of the above mentioned novel derivatives of cephalexin. These purposes are achieved by the cephalexin derivatives according to the invention which consist in a methylol derivative of cephalexin having general formula

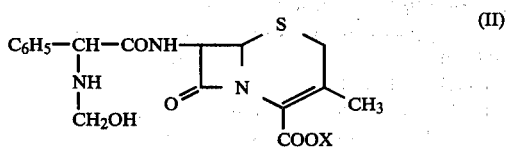

wherein X is an alkali metal, or the organic nitrogen containing cation of a generic basic aminoacid.

Preferred, although non limiting examples of these cations comprise sodium and the cations of lysine and arginine.

It has been surprisingly found that the methylol derivatives of cephalexin, as above defined, not only maintain the wide spectrum of antibiotic activity of cephalexin even against gram-negative germs and furthermore are not inactivated by the staphilococcic penicillinase, but, unlike cephalexin, are perfectly soluble in water and moreover, unlike the to date known derivatives of cephalexin, provide practically neutral and injectable solutions.

The methylol derivatives of cephalexin as represented by the structural formula (II) are prepared through a process essentially comprising the following steps:

(a) a water suspension of cephalexin is contacted, under intense stirring and at a temperature of between about 5° C. and 10° C., with a solution of formaldehyde, giving a phase comprising a methylol derivative having general formula:

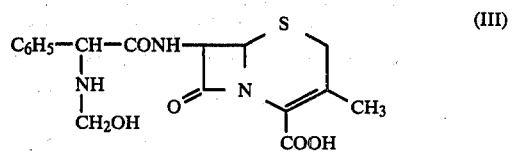

(b) the reaction mixture obtained in step (a) is contacted with a water solution of an inorganic base having formula XOH, wherein X is a cation selected amongst the cations of alkali metals, or with a solution of a basic aminoacid, giving a solution of the methylol derivative.

The solution thus obtained in the preceeding step (b) can be treated in a lyophilization step to obtain a solid product of formula II, which is equally perfectly soluble in water.

The following examples illustrate the preparation of two methylol derivatives according to the present invention.

EXAMPLE 1

Lysine salt of 2-N-methylol-cephalexin 18 g of monohydrate cephalexin were suspended in 100 mls of distilled water at the temperature of 5° to 10° C.

By maintaining the temperature of the suspension within the above indicated limits, 3.8 mls of a 40% formaldehyde solution were added dropwise under vigorous stirring. A continuous stream of pure nitrogen was meanwhile bubbled through the reaction mixture.

After about 10 minutes of stirring under the above conditions, a 50% solution of 14 g of lysine base was slowly added. The reaction mixture was little by little solubilized and the pH final value of the resulting solution was 7.5. The volume of the obtained solution was brought to the end value of 150 mls by adding cold distilled water. It was then sterile filtered and frozen in a prefreezer at −70° C. and finally lyophilized.

A powder having a colour tending to yellow was obtained with the following chemical and physical properties:

appearance: microcystalline powder of colour tending to yellow;
solubility: cold soluble in water and little soluble in absoluble alcohols;
cephalexin microbiological title: 99 to 100% of theoretical value.

The spectrum of nuclear magnetic resonance is that of the enclosed FIG. 1.

EXAMPLE 2

Sodium salt of 2-N-methylol-cephalexin

The procedure of example 1 was repeated, except that, instead of the lysine solution, 46 mls of a 1N NaOH solution were added.

The thus obtained solution had a final pH of 7.1.
Chemical and physical properties:
appearance: light yellow microcrystalline powder;
solubility: highly water soluble, little soluble in ethanol and absolute alcohols;

cephalexin microbiological title: 99 to 102% of the theoretical value.

Figure 2:
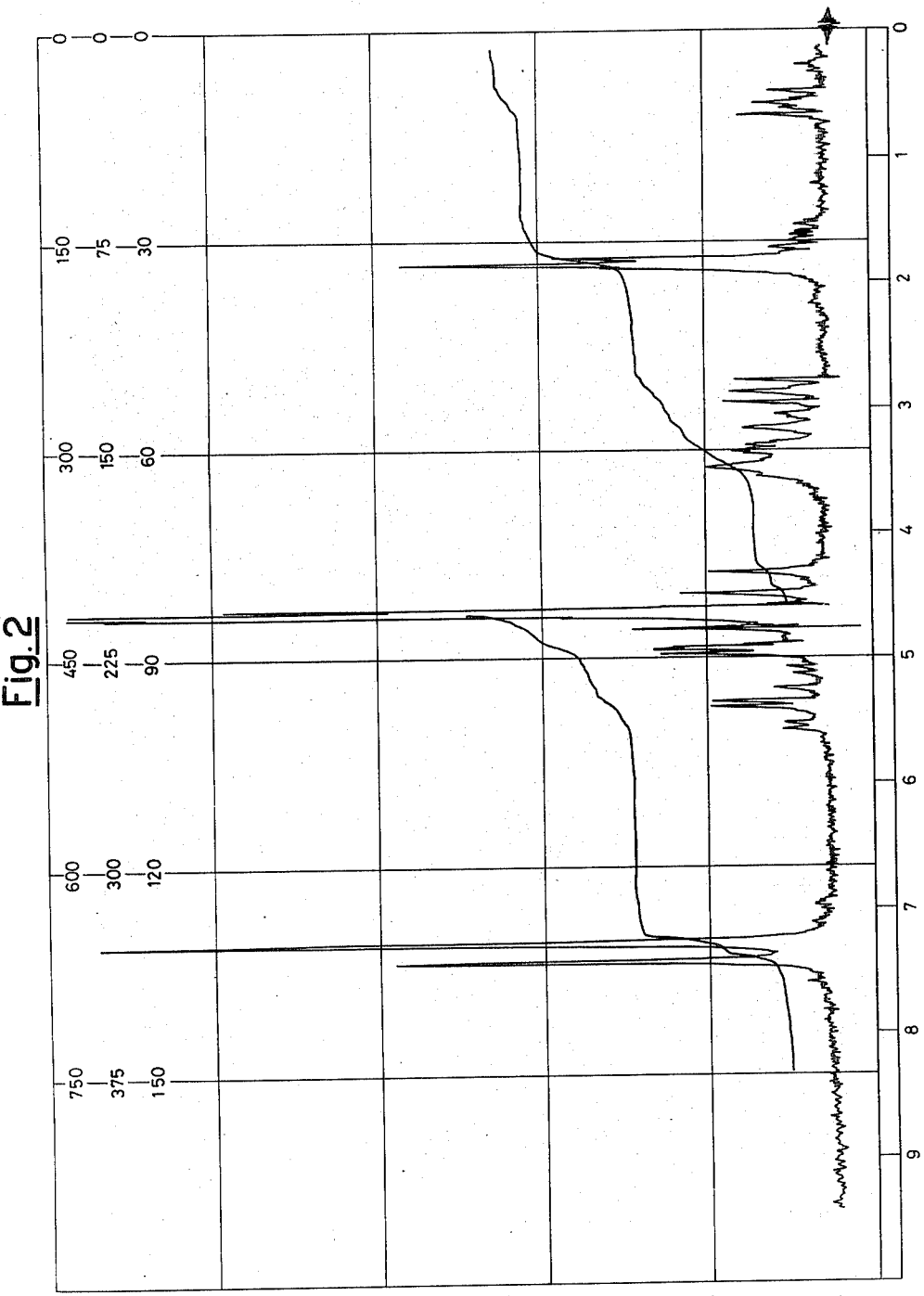

The spectrum of nuclear magnetic resonance is that of the enclosed FIG. 2.

Pharmacological and clinical tests have been carried out with the compounds of the invention and the results related to the lysine salt of 2-N-methylolcephalexin are hereinafter reported for illustrative purpose.

(A) Toxicity.

In the mouse
-by intraperitoneal administration: $LD_{50} = 3.1$ g/kg
-by oral administration: $LD_{50} = $ greater than 4 g/kg In the rat per os the $LD_{50}$ is also greater than 4 g/kg (B) Haematic levels The concentrations of lysine salt of methylol cephalexin (substance A) in the blood have been checked (after oral administration) in the human being, in comparison with a reference compound namely cephalexin monohydrated (substance B), with the following results:

after 1 h — A = 1.3 B
after 3 h — A = 3.5 B
after 6 h — A = 24.0 B

The urinary elimination within 24 hours is 87% for the substance (A) and 90.5% for the substance (B).

From the pharmacokinetic data it can be concluded that:

(1) the substance A gives at peak time levels 3.5 greater than those of substance B;
(2) the presence in the blood stream is higher for the substance B and actives concentrations are detected more than 6 hours after the administration;
(3) the area under the curve (AUC) for the substance A is about two times that of substance B.

I claim:

1. Methylol derivative of cephalexin having the formula:

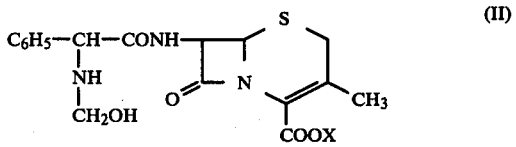
(II)

wherein X is an alkali metal or the organic nitrogen containing cation of a basic aminoacid.

2. Methylol derivative according to claim 1, characterized in that the cation X is sodium.

3. Methylol derivative according to claim 1, characterized in that the cation X is the cation of a basic aminoacid selected in the group comprising lysine and arginine.

4. A process for the preparation of a methylol derivative of cephalexin having the formula:

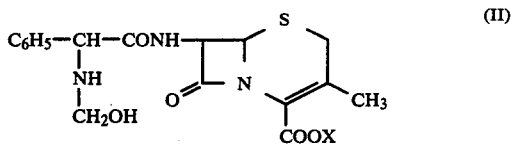
(II)

wherein X is an alkali metal or the organic nitrogen containing cation of a basic aminoacid comprising the following steps:

(a) a water suspension of cephalexin is contacted under under intense stirring, at a temperature of between about 5° and 10° C., with a formaldehyde solution, obtaining a phase comprising a methylol derivative having the formula:

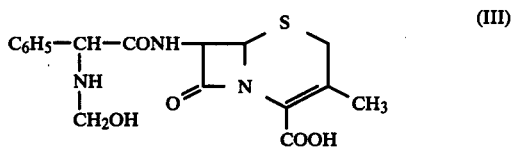
(III)

(b) the reaction mixture obtained in the step (a) is contacted with a water solution of an inorganic base having the formula XOH wherein X is an alkali metal cation, or with a solution of a basic aminoacid, thus obtaining a solution of the methylol derivative (II).

5. A process according to claim 4 further comprising the step of subjecting the solution of the step (b) to lyophilization, thus obtaining a solid product having formula (II).

6. A process according to claim 4, characterized in that said base is sodium hydroxide.

7. A process according to claim 5, characterized in that said base is sodium hydroxide.

8. A process according to claim 4, characterized in that said basic aminoacid is selected from the group consisting of lysine and arginine.

9. A process according to claim 5, characterized in that said basic aminoacid is selected from the group consisting of lysine and arginine.

* * * * *